United States Patent [19]

Eberly et al.

[11] Patent Number: 5,073,029

[45] Date of Patent: Dec. 17, 1991

[54] MULTISOURCE DEVICE FOR PHOTOMETRIC ANALYSIS AND ASSOCIATED CHROMOGENS

[75] Inventors: James P. Eberly; Ralph A. Magnotti, Jr., both of Cincinnati, Ohio

[73] Assignee: EQM Research, Inc., Cincinnati, Ohio

[21] Appl. No.: 481,450

[22] Filed: Feb. 16, 1990

[51] Int. Cl.⁵ .............. G01N 21/59; G01N 1/10; G01N 33/48
[52] U.S. Cl. .................... 356/432; 356/39; 356/246; 356/436; 422/82.05; 422/82.09
[58] Field of Search .............. 356/39, 40, 246, 432, 356/435, 436; 422/50, 68.1, 82.05, 82.06, 82.07, 82.08, 82.09; 436/806

[56] References Cited

U.S. PATENT DOCUMENTS

| | | | |
|---|---|---|---|
| 3,910,701 | 10/1975 | Henderson et al. | 356/39 |
| 4,357,105 | 11/1982 | Loretz | 356/40 |
| 4,431,307 | 2/1984 | Suovaniemi | 356/246 |
| 4,591,550 | 5/1986 | Hafeman et al. | |

Primary Examiner—Vincent P. McGraw
Assistant Examiner—LaCharles P. Keesee, II
Attorney, Agent, or Firm—Cooley Godward Castro Huddleson & Tatum

[57] ABSTRACT

An optoelectronic device is provided which permits rapid sequential measurement of the optical density of multiple samples. The device employs a plurality of light-emitting diodes (LEDs) as light sources and a plurality of photodiodes as light detectors. In a preferred embodiment, arrays of LEDs paired with photodiodes are adapted to measure the optical density of samples contained in multiwell plastic plates (microplates) conventionally used for immunoassays.

12 Claims, 7 Drawing Sheets

MULTISOURCE DEVICE FOR PHOTOMETRIC ANALYSIS AND ASSOCIATED CHROMOGENS

FIELD OF THE INVENTION

One aspect of the invention pertains to optoelectronic devices adapted for rapid, reproducible, and sequential measurement of the optical density of multiple samples. The devices disclosed in the present application employ a plurality of light-emitting diodes (LEDs) as light sources and a plurality of photodiodes as light detectors. In a preferred embodiment, arrays of LEDs paired with photodiodes are adapted to measure the optical density of samples contained in multiwell plastic plates (microplates) conventionally used for immunoassays.

A second aspect of this invention pertains to a process and a kit for using modified chemical reactions in enzyme-linked immunosorbent assays (ELISAs). These modified reactions produce chromophores which have improved light-absorbing properties when used for ELISAs, and are especially adapted for use with the microplate measuring device of the first aspect of this invention.

DESCRIPTION OF THE PRIOR ART

For many years optoelectronic devices have been used for measuring the optical density (absorbance) of solutions. The absorbance of a solution of a light-absorbing chromophore can be used to determine its concentration, according to the Beer-Lambert relationship, $A = \epsilon b c$; where $A$ = absorbance, $\epsilon$ = chromophore absorptivity, $b$ = pathlength, and $c$ = chromophore concentration. Chromophores can thereby be measured directly from their solution absorbance, or they can be linked by further chemical reactions to other non-chromophores to indirectly measure the concentration of non-absorbing species. In the ELISA technique a non-absorbing antibody to a specific analyte linked to a chromogenic enzyme forms a complex with the analyte. After separation, the amount of analyte, which is proportional to the amount of enzyme-produced chromophore, is determined by absorbance. See, e.g., Engvall, Methods in Enzymology Vol. 70 (1980) pp. 419–439, and Ishikawa, Clinical Biochemistry 20 (1987), pp. 375–385.

Because of the popularity of the ELISA technique, numerous commercially available instruments have been developed which read the absorbance of ELISA solutions in microplates. The configurations of commercial microplate readers are similar. Typically, the focused output of a single incandescent light source is passed sequentially through a narrow-band filter, the solution being analyzed, and then through the transparent microplate, after which the unabsorbed light impinges on a photodetector, which produces an analog signal in proportion to the light intensity. Using standard electronic components, this analog signal is normalized against the signal obtained in the absence of analyte, to obtain an optical transmittance, which is further converted electronically to absorbance, which is the negative logarithm of transmittance. The 96 wells of the microplate are separately read by moving each well in turn through the filtered source beam by a mechanical carrier which moves the microplate. On less sophisticated (manual) models, the carriage of the microplate reader is moved by hand, whereas in more costly advanced instruments, a motorized drive mechanism automatically moves the microplate through the light beam, resulting in greater convenience, speed, and precision of measurement.

The technology of conventional microplate readers has significant disadvantages. A key weakness is the reliance on mechanical movement of the plate, which requires costly precision drive mechanisms to insure rapid reproducible movement. In particular, kinetic measurement of the rate of chromophore production, which can provide useful information, requires the ability of the microplate reader to perform rapid, precisely timed measurements in each of the 96 microplate wells, in a reproducible manner. This kinetic capability is precluded for manual readers, and is available on only the most sophisticated instruments. With the latter, such as the Molecular Devices Vmax and the Bio-Rad MR5000, carriage movement has ben reduced by splitting the source beam with fiber optics so that an entire row or column of the microplate wells can be read approximately simultaneously, thereby increasing speed of analysis.

Another drawback of conventional instruments is that they consume relatively large amounts of electric power required for operation of the electromechanical carriage and incandescent light source, thereby precluding battery operation and limiting their portability. In addition, the carriage mechanism and source (light bulb) are relatively fragile and susceptible to breakdown, limiting their ruggedness for use in the field. This fragility often necessitates the use of a service contract for the instrument, and certain parts, such as the bulb, have a limited life and must be replaced regularly. This requirement for service and supply also limits the portability and field operation of conventional microplate readers. This is particularly problematic when performing clinical or environmental analysis in rural areas, where line power is not available and resupply with replacement parts difficult.

The use of only solid-state components is a familiar strategy in designing a spectroscopic instrument for low power consumption and good shock resistance. For this reason, solid-state electroluminescent devices such as LEDs are sometimes substituted for light bulbs as spectroscopic sources. LEDs are shock-resistant and inexpensive. With rated lifetimes of about 100 years, LEDs are virtually maintenance-free.

However, due to serious limitations, LEDs have only occasionally been used in spectroscopic instruments for measuring absorbance. The most significant limitation of LEDs relative to incandescent sources is that LEDs produce weak emissions distributed over a limited number of narrow wavelength ranges. This limitation has generally restricted LEDs to absorbance measurements on strongly absorbing, broad-band chromophores.

As an example, Loretz U.S. Pat. No. 4,357,105 has described a photometer employing a single green LED light source, a long-wavelength cutoff filter, a photodiode detector, and associated electronic signal amplifier and readout display. The Loretz patent particularly teaches that the battery power supply must be stabilized so that the power going to the LED is maintained at a constant level, thereby maintaining constant brightness. Loretz also provides means for manually adjusting the gain of the photodetector to keep the signal within the display scale. Since only a single LED, photodetector, and sample compartment are provided, only one sample may be measured at a time. The resulting instrument is adapted especially for measuring hemoglobin, which has an intense, broad-band absorptivity within the restricted wavelength region emitted by the filtered LED.

As an example of a different approach, Henderson U.S. Pat. No. 3,910,701 has described an instrument which employs a plurality of LEDs, each LED emitting light of either a longer or shorter wavelength. The two types of LEDs are arranged in a ring around a central photodetector, and are pointed at a spot above the photodetector. The surface of the sample is placed at that spot, so that light reflected from the sample surface will strike the photodetector. The two different types of LEDs are pulsed alternately, so that light of different wavelengths is reflected alternately. The ratio of signals striking the photodetector at alternate periods is therefore a measure of the differential reflectance of the sample. Because the Henderson instrument employs two different sets of LEDs, it requires a means of compensating for the different intensity of light emitted by the two sets. This is accomplished by providing a manually variable impedance to one set of LEDs, so that the intensity of light emitted from the two sets may be equalized. As in the Loretz instrument, the Henderson instrument contemplates measuring only a single sample at a time. Accordingly in most embodiments the instrument employs only a single photodetector. An alternative embodiment employs two photodetectors, one for transmitted light, and the other for reflected light, but the two photodetectors are still confined to measuring a single sample. The Henderson invention thus compensates for the relatively weak intensity of emission from each LED by directing multiple LEDs onto a single sample, and compensates for the restricted wavelength range of a single LED by directing LEDs of different wavelength emissions onto the single sample.

In a third example, Bordier and Ryter (Analytical Biochemistry 152:113-118, 1989) have described an instrument for measuring the transmittance of dot blots on an analytical membrane. This instrument employs four LED-photoresistor detector pairs mounted in a row. The operator manually positions the membrane sheet so that the colored sample spots are placed over the LEDs. The operator then manually switches the LED power and detector circuitry to one LED-photoresistor pair, reads the resistance from a voltmeter across a measurement resistor in series with the photoresistor, and manually records the resistance. The operator then manually switches to the next LED-photoresistor pair and repeats the process. After a maximum of four readings the operator must manually reposition the membrane to read the next four sample spots, and so on. The resistance values are then manually converted with a hand-held calculator to yield absorbances. Clearly, this device is very tedious and slow, and is not suitable for routine processing of the large number of samples which might be encountered in a clinical, research, or industrial laboratory.

Accordingly, it is one object of the present invention to provide a microplate reader which is battery-operable and portable.

It is yet a further object of the present invention to provide a plate reader which reads an entire microplate without plate movement during such reading.

It is yet a further object of the present invention to provide a microplate reader which contains no electromechanical parts so as to avoid instrument failure in the event of a breakdown of such parts.

It is yet a further object of the present invention to provide a microplate reader which does not routinely require replacement parts (such as bulbs) during the life of the instrument.

It is yet a further object of the present invention to provide a microplate reader which can analyze all of the samples in a microplate at precisely timed intervals in a rapid and reproducible manner, producing absorbance data suitable for kinetic analysis.

It is yet a further object of the present invention to provide chemical processes and kits for generating chromophores for ELISAs which have enhanced light absorbance at the wavelengths emitted by the green LED used in a favored embodiment of the above microplate reader, and which chromophores are thereby especially adapted for use with the said microplate reader. The process comprises adding a color-shifting reagent such as 3,3'-dimethylnaphthidine to a conventional peroxidase-substrate reaction mixture.

SUMMARY OF THE INVENTION

We have developed an all-solid-state device which achieves substantially all of the relevant objectives stated above. Specifically the microplate reader of the present invention employs a plurality of LED-photodiode pairs as the light source-detector combination for absorbance measurement. One LED-photodiode pair is provided for each sample well of the microplate, and the array of LED-photodiode pairs is spatially configured to match the array of microplate wells. In one preferred embodiment, each LED is mounted below an aperture and optical filter and directly below the transparent plastic surface of a corresponding microplate well. The emission from the said LED passes through the said aperture and filter and passes through the assay solution resident in the microplate well. Each said photodiode of the said pairs is correspondingly mounted above the sample well and measures the LED emission exiting from the sample solution. The photodiode then converts the emission to an electrical signal which is amplified and passed to an attenuator which adjusts for variability in baseline signal output between LED-photodiode pairs. The adjusted signal is then passed through an electronic filter to an analog-to-digital converter, which converts the signal into a numerical value. A microprocessor then computes absorbance values from numerical values by comparing signals from the LED-photodiode pair in the absence of LED emission ("0%" transmittance) and in the absence of analyte (100% transmittance).

In its broader aspects, this invention can be adapted to perform optical density measurements on numerous types of samples in addition to solutions contained in microplate wells. With no or minor modification it can measure dot-blots on analytical membranes, or stained biochemical samples in gels. By employing smaller and more tightly packed arrays of LEDs and photodetectors, the resolving power of the device is increased, and irregularly spaced samples may be read as well as those in a regular grid. For example, this high-resolution array permits direct reading of stained two-dimensional gels, in which colored sample spots may be found on any position on the two-dimensional gel or membrane. Because of this aspect of the invention, the term "plurality of samples" must be understood to refer not only to a plurality of discrete samples in individual wells or cuvettes, but also to any sample, whether singular or plural, on which it is desirable to make measurements of its absorbance at a plurality of spatially distinct positions.

We have also developed a chemical process for generating a novel chromophore for ELISAs. The said chromophore is especially adapted for use in a preferred embodiment of the microplate reader described above. That embodiment uses the so-called "true green" LED, which has a dominant wavelength of about 555 nm. Previously known ELISA chromogenic reactions are not optimally suited for use with the true green LED-source microplate reader because the resulting chromophores absorb weakly at 555 nm, thereby reducing measurement sensitivity and increasing the polychromatic error of measurement. The chromophores of the present invention, however, has maximal absorbance in the region of 555 nm. Generation of the said chromophores is based on our discovery that the yellow acid-stable 2-electron oxidation product of the peroxidase substrate 3,3',5,5'-tetramethylbenzidine can be coupled with the electroactive chromogens MNAP (3,3'-dimethylnaphthidine) and TMPD (N,N,N'N'-tetramethyl-p-phenylenediamine), to produce stable chromophores with enhanced absorptivity near 550 nm.

DETAILED DESCRIPTION OF THE INVENTION

Figure 1:
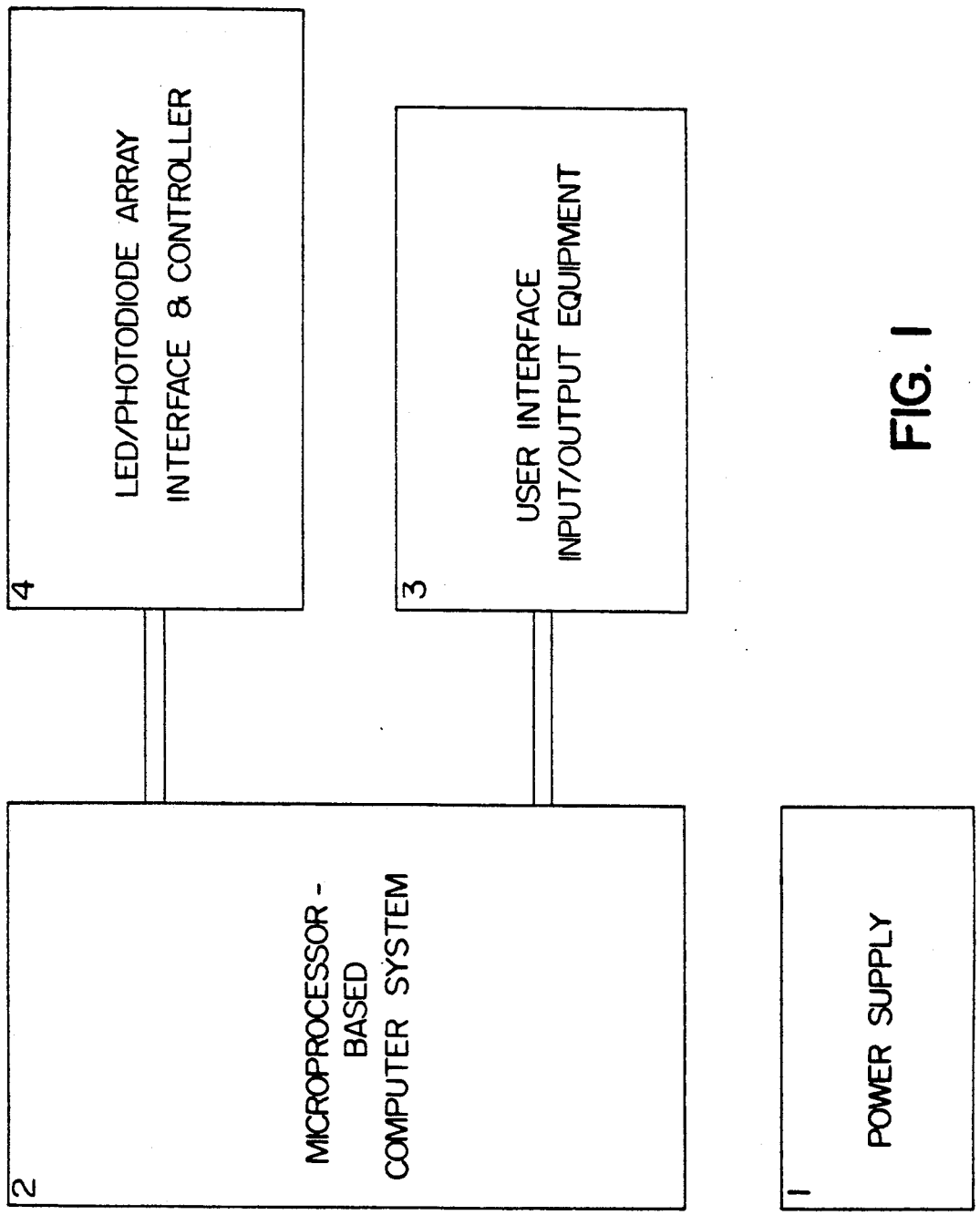
FIG. 1 is a block diagram of the basic subsystems of the instrument.

FIG. 1 shows the essential subsystems of the photometric device of this invention. The power supply (1), regulates the incoming voltage as supplied by either a battery pack or a power line supplied direct current adapter. The power supply produces: 1..) a +5 volt digital power source, 2.) a +5 volt analog power source, and 3.) a −5 volt analog power source. Any one of many possible power supply designs would prove adequate to run this invention on a power line supplied direct current adapter. To enable battery operation of this invention, a power supply with high power conversion efficiency and low quiescent current is necessary. In a preferred embodiment of this invention, the Harris Semiconductor ICL7663S voltage regulator and ICL7660S voltage inverter provide a highly optimal power supply design. The microprocessor-based computer system (2), coordinates the actions and responses of this invention. Although virtually any of the dozens of available microprocessor-based computers could perform the required functions satisfactorily, a system constructed around the Hitachi 64180 microprocessor is highly desirable. The 64180 is a low current microprocessor that is capable of addressing one megabyte of main memory and contain several on-chip support circuits useful in implementing this invention. The low operating current of the 64180 facilitates battery operation. Its ability to address one megabyte of main memory allows highly sophisticated software packages to be executed on this invention. The several on-chip support circuits of the 64180 provide mechanisms for communicating to both a remote computer system and a remote printer. The support circuits of the 64180 also allows the precision timing generation necessary to this invention. In addition to the 64180 microprocessor, the microprocessor-based computer system of this invention contains: 1.) an 8 kilobyte non-volatile static random access memory with a non-volatile clock calendar function, 2.) a 32 kilobyte static random access memory, 3.) a user changeable memory cartridge which contains up to 512 kilobytes of erasable programable read only memory, and 4.) interface circuitry to permit communications with the other subsystems of this invention. The user interface input/output equipment (3), allows this invention to interact with a human operator. This equipment includes: 1.) an alphanumeric liquid crystal display, 2.) a 24 key membrane style keypad, 3.) a piezo electric audible sounding device, and 4.) RS-232 interface circuitry to both a remote printer and a remote computer. A specific innovation of this invention is the LED/photodetector array interface & controller (4) which shall be subsequently described in greater detail.

Figure 2:
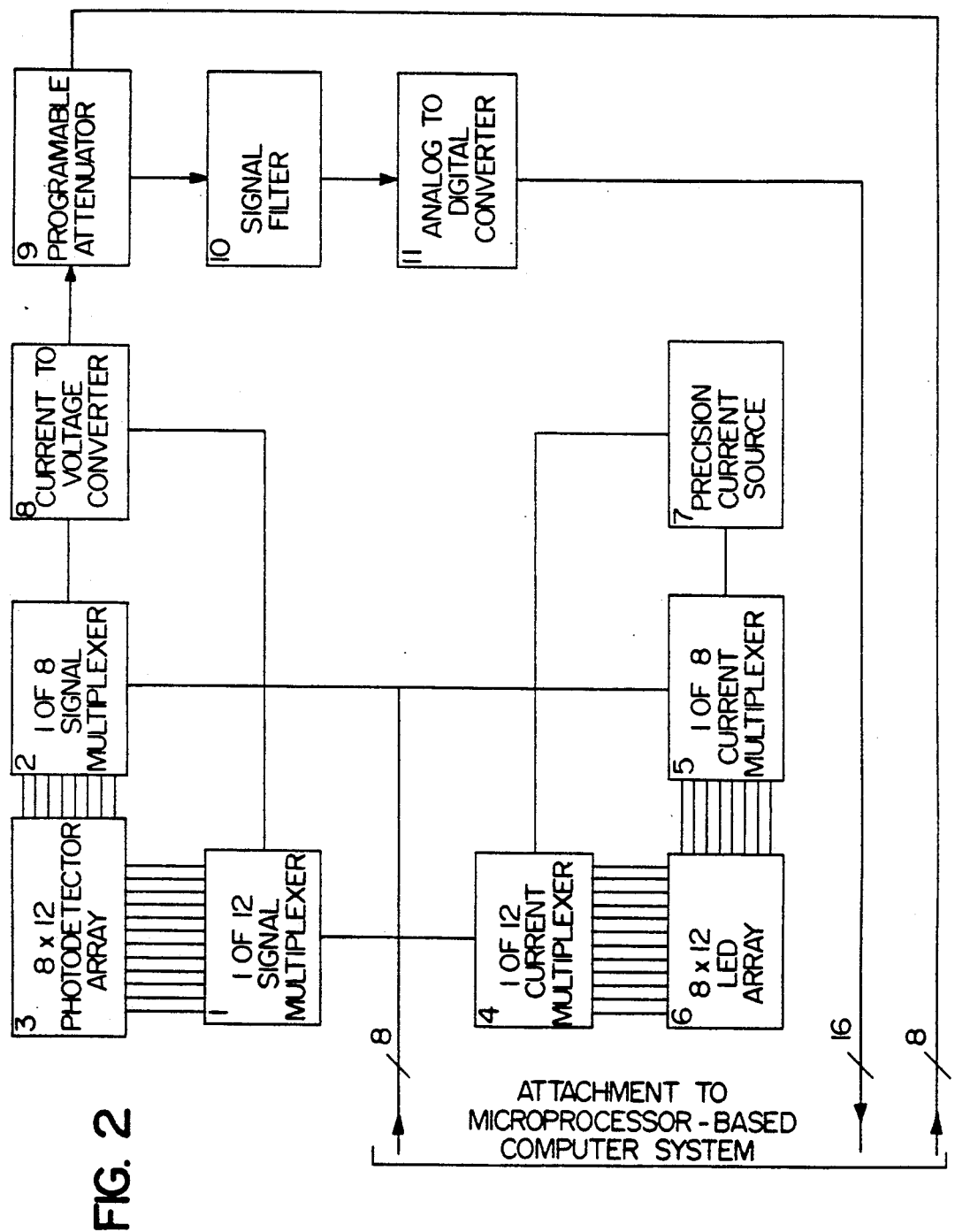
FIG. 2 is a block diagram of the electronic circuitry adapted for pulsing the LED array, detecting the emitted light after passage through the samples using the photodiode array, and electronically processing the resulting signals.

FIG. 2 shows the main components of the LED/photodetector array interface & controller. The collection of circuits performs the following functions: 1.) selects a photodetector and its corresponding LED from among the array of such LED/photodetector pairs, 2.) properly drives the selected LED in such a way as to emit a precision light pulse, 3.) properly converts the very small current signal received from the selected photodetector into a suitable analog voltage signal, 4.) attenuates the received signal so that a majority of the ADC's (Analog to Digital Converter) input range may be utilized for each of the LED/photodetector pairs, 5.) conditions the post-attenuator signal into a form suitable for the ADC, and 6.) converts the analog signal into a digital form for use by the microprocessor-based computer system.

A group of control signals from the microprocessor-based computer system goes to both the signal and current multiplexers. A 1 of 12 signal multiplexer (1)

selects the desired column of photodetectors and a 1 of 8 signal multiplexer (2) selects the desired row of photodetectors. By specifying both the row and column in the 8×12 photodetector array (3), a single photodetector is addressed. In a similar fashion, a 1 of 12 current multiplexer (4) selects the desired column of LEDs and a 1 of 8 current multiplexer (5) selects the desired row of LEDs. Again, by specifying both the row and column in the 8×12 LED array (6), a single LED is addressed. In the preferred embodiment where the device is a microplate reader, 1 of 8 and 1 of 12 multiplexers are appropriate. These dimensions clearly correspond to the 8 rows and 12 columns of optoelectic components required to read a standard 96-well (8×12) microplate. Naturally, for other applications to which this invention is applicable, a different number of optoelectric components may be required and the dimensionality and number of the multiplexers should be adjusted accordingly. In a preferred embodiment, the signal multiplexers are CMOS devices having low input current leakage so as not to distort the received photodetector signal and the current multiplexers are high gain devices so as not to distort the LED drive current. Typical devices conforming to these descriptions are the RCA CD4051 CMOS signal multiplexer and the Sprague UDN2983A and UDN2003A current multiplexers.

To insure the emission of a precision light pulse from the LED, a precision current source (7) is necessitated in that the power of the light emission is directly proportional to the applied current. Any inprecison or instability in the current source will be directly propagated to the LED light pulse. A current stability of greater than 0.1% is necessary to enable this invention to accurately measure an optical transmittance to one part per thousand. The transient stability to pulsed loads and the thermal stability of the semiconductor devices to self-heating are of particular importance in the design of the precision current source. In a preferred embodiment of this microplate reader, the said precision current source is constructed to generate 20 milliamperes.

The current to voltage converter (8) transforms the very small (100 nanoamperes full scale) output current of the selected photodetector into a voltage (between 0.2 volt and 1 volt full scale) suitable for subsequent signal processing and analog to digital conversion. An operational amplifier with an extremely low input offset current and extremely high input impedance is necessary. In a preferred embodiment of this invention the current-to-voltage converter is constructed using an RCA CA3140 or a Harris Semiconductor ICL7611 operational amplifier. This converter should also be purposely bandwidth-limited to avoid amplification of high frequency noise sources.

The voltage signal from the current-to-voltage converter passes to a programable attenuator (9). The programable attenuator provides a means for compensating for the difference in output signals among the LED/photodetector pairs. One obstacle to producing a multiple LED-source instrument is that the individual LEDs generate different amounts off luminous intensity for a given pulse power, so that the brightest LED in a purchased lot may be brighter than the dimmest by a factor of 3. Similarly, the individual photodetectors in the said array will vary in the level of dark current which they pass and in their sensitivity to a given amount of illumination. Therefore the magnitudes of the signals coming from the plurality of LED/photodetector pairs are not commensurate with each other and must be normalized.

Although normalization could come at a later stage of the measurement process, such as adjusting the values transmitted to the microprocessor-based computer system via a software procedure, the use of a programable attenuator at the analog signal stage is preferable. This is because the signals from the plurality of LED/photodetector pairs are adjusted so that each said signal can take full advantage of the dynamic range of the ADC, thereby increasing the precision of the measurements.

The output signal from the programmable attenuator is passed to a signal filter (10). The signal filter serves to suppress high voltage transients which are generated when the signal multiplexers switch photodetectors. Additionally, a low-pass filter is employed to remove unwanted high frequency noise from the analog signal to be subsequently sampled. Such circuits are well-known in electronics work, and a large number of alternative designs are possible. A suitable filter circuit may be constructed of passive elements such as resistors, capacitors, and detectors.

The signal next passes to an analog-to-digital converter (11). In a preferred embodiment of the microplate reader, an integrating type of ADC is employed. The analog signal is integrated over an integer multiple of the power line period (1/60 second or 1/50 second) to highly reduce power line induced noise. Specifically, this period of integration is generated from a quartz crystal oscillator to allow rejection of power supply induced noise even while operating from batteries. The integration function also acts as a signal averaging mechanism which lessens the influence of other extraneous sources of noise. The analog signal is converted with a digital precision of 1 part per 4096. In addition to the 12 converter output code lines, a signal polarity indicating line, and an over-range indicating line are sent to the microprocessor-based computer system for further analysis. In a preferred embodiment of this invention, the Harris Semiconductor ICL7109 integrating ADC is employed.

The method by which the microprocessor-based computer system interacts and commands the LED/photodetector controller & interface is a specific innovation which enables the correct operation of this invention. The software to operate the LED/photodetector controller & interface is based upon: 1.) an algorithm to determine the appropriate programmable attenuator setting the for each of the LED/photodetector pairs, 2.) an algorithm to calibrate the LED/photodetector pairs, 3.) an algorithm to acquire raw data from the LED/photodetector pairs, 4.) an algorithm to determine the transmittance—and hence the absorbance—of samples interposed between each of the LED/photodetector pairs, 5.) a method to allow the stable functioning of the LED-source units, and 6.) an algorithm to compensate for the individual long-term drift factor of each LED in the LED/photodetector array.

After the initial construction of said microplate reader, a software procedure to determine the appropriate programmable attenuator setting for each of the LED/photodetector pairs is executed. This procedure is based on an algorithm which conducts a data acquisition cycle (explained below) for each LED/photodiode pair and then adjusts the attenuator constant a[i] for that LED/photodetector pair in such a fashion as to obtain an ADC output value of approximately 3800 parts per 4096. Using a successive approximation technique, the correct 8-bit programable attenuator constant may be obtained in 8 of these read and adjust cycles. After the correct values of a[i] are obtained for each of the LED/photodetector pairs, an "attenuator table" consisting of the programmable attenuator constants is stored in the non-volatile memory of the microplate reader. In addition, an "attenuator checksum" is stored in non-volatile memory to allow the validity of the attenuator table values to be subsequently determined. When the said invention is turned on for normal use, the microprocessor-based computer system will access the attenuator table and validate the attenuator checksum. If the checksum is correct, normal operation will result; however, if the checksum does not agree with the values stored in the attenuator table, the above program will be re-executed to build this table for subsequent operation. This allows the unit to remain functional in spite of a system crash.

When the microplate reader is turned on, a calibration program is automatically executed to calibrate the LED/photodetector pairs. This program is based on an algorithm that obtains a full scale value and a zero scale value for each LED/photodetector pair in the absence of a test sample. Operationaly, a data acquisition cycle (explained below) is conducted without a microplate in the instrument and each ADC output value is stored as F[i] in a "full scale table". These F[i] represent the 100% transmittance values for each of the LED/photodetector pairs. Next, a read cycle is conducted with the LED-source turned off. Each ADC output value is stored as Z[i] in a "zero scale table". These Z[i] represent the 0% transmittance values for each of the LED/photodetector pairs. In addition to this calibration procedure executing when the microplate reading is turned on, this same procedure may be activated at any time by the instrument user in order to force a re-calibration.

A program based on a data acquisition algorithm is used extensively in said invention. This algorithm specifies applying the following steps to each of the LED/photodetector pairs in succession: 1.) select the LED/photodetector pair, i, from which to acquire data, 2.) load the programmable attenuator with the value of a[i], 3.) turn on the LED drive current, 4.) allow the LED, the precision current source and the current-to-voltage converter to stabilize, 5.) start the integrating ADC, 6.) wait for the completion of the ADC integration period, 7.) obtain the ADC output value, 8.) store this output value appropriately, and 9.) turn off the LED drive current.

The transmittance of every sample well of a microplate is calculated by a program based on the following algorithm: 1.) execute a data acquisition cycle—with the sample containing microplate in place—and record the ADC output value of each sample as D[i], 2.) apply the mathematical relationship $T[i] = (D[i] - [i])/(F[i] - Z[i])$ where T[i] is the transmittance of sample i and the other values are as previously elucidated. From the transmittance value T[i], the absorbance value A[i] may be calculated automatically using the familiar relation: $A[i] = -\log 10(T[i])$.

In a further aspect of the invention, a method for stabilizing the light output of the said LEDs is employed. The intensity of the emission from any LED varies with the temperature at which the semiconductor die is operated. During a period in which current flow through the LED causes light emission, the LED heats up and its efficiency of converting electrical energy to radiant energy changes. When an LED is pulsed, it heats during the pulse but cools during the interval between pulses. In a pulsed instrument using LED light sources, the emitted light intensity may vary as a function of pulse interval and duration. In order to compensate for the change in efficiency of emission at long intervals between pulses, the LEDs of the microplate reader, in a preferred embodiment, are subjected to short heating pulses at regular periods when the instrument is not being used for data acquisition cycles. By keeping the time average of the heating pulse approximately equal to the time average of the sampling pulses, the net power influx to the LEDs is kept constant. In this manner the LED dies are maintained at a nearly constant temperature and thus their sample-to-sample light emission is closely regulated. In a preferred embodiment of this invention, the heating pulses are between 100 and 1000 microseconds in duration.

Although the heating pulse strategy serves to greatly stabilize the light emission of the LEDs, slight long term (1 hour) drifts may still be observed due to slight manufacturing differences in both the LED dies and the thermal conductivity between the LED die and the enclosing plastic package. In a highly preferred embodiment of this invention, after the initial construction of said microplate reader, a program is executed to adjust the individual heating pulse duration of each LED in the LED/photodetector array. This program is based on the following long-term compensation algorithm. A "drift table" is built in the non-volatile memory of this invention such that each entry d[i] of the table is given the same initial values. This non-critical initialization value should translate to a heat pulse time of around 500 microseconds. Next, a data acquisition cycle is completed and the ADC output values stored. After a delay of several minutes, another data acquisition cycle is completed and the ADC output value is compared to that of the prior acquisition cycle. If the difference in ADC output values corresponding to the same LED/photodetector pair has increased between cycles, then the drift table value corresponding to that LED/photodetector pair is increased. This will minutely increase the average power into the LED-source and drive down the efficiency of the LED, causing a very slight long term reduction in light emission. Conversely, if the difference in ADC output values corresponding to the same LED/photodetector pair has decreased between cycles, then the drift table value corresponding to that LED/photodetector pair is decreased. This will minutely decrease the average power into the LED-source and drive up the efficiency of the LED, causing a very slight long term increases in light emission. This process of comparing successive samples of several minute intervals is continued, and the drift table adjusted, until the instrument exhibits no change in the ADC output values corresponding to any of the LED/photodetector pairs over several consecutive hours. In addition to the drift table, a "drift checksum" is stored in non-volatile memory to allow the validity of the drift table values to be subsequently determined. When the said invention is turned on for normal use, the microprocessor-based computer system will access the drift table and validate the drift checksum. If the checksum is correct, normal operation will result; however, if the checksum does not agree with the values stored in the drift table, a default drift constant will be used and the instrument user warned of the lost table. This allows the unit to remain functional in spite of a system crash and the above program may be user-invoked to rebuild a lost drift table.

In a preferred embodiment, the said photodetectors in the array are photodiodes, which have favorable sensitivity to visible light and rapid response times compared to other solid state photodetectors such as photoresistors and photovoltaics. The preferred photodiodes have integral infrared filters covering their photoreceptive surface. Such filters screen out the unwanted infrared emissions which are incidentally emitted by many LEDs. One particular such photodiode which is especially preferred in the microplate reader is the Hammamatsu S1133. In general all of the photodetectors in the said array will be powered continuously while the unit is in operation, but the signal from only one of them will be directed into the amplifier at any given instant.

As another means to reduce stray light effects, the naturally divergent beam from each said LED is collimated, so that a major portion of the beam is confined to the sample-containing portion of the microplate well. In the absence of a collimation means, the light beam emitted from each LED tends to be reflected from transparent surfaces of the microplate other than the circular window—the bottom of each microplate well—which is oriented perpendicular to the LED emission. Such reflected light can strike the photodetector without having passed through the sample, thereby distorting measurement.

Figure 3:
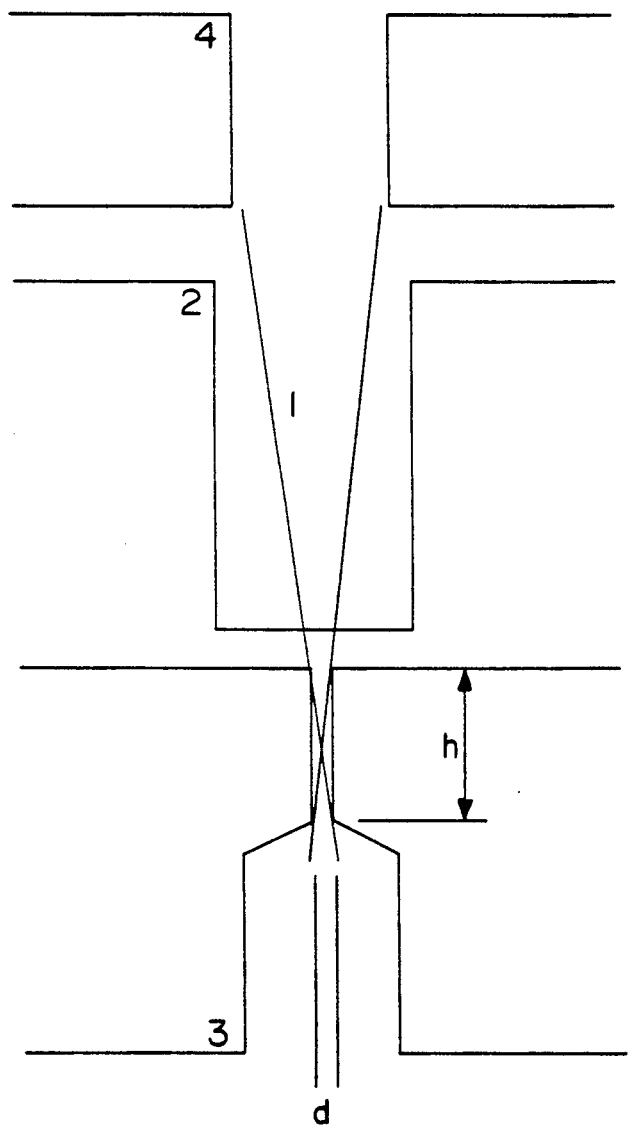
FIG. 3 is a cross-sectional view showing a single pair of mounting holes for an LED-photodiode pair, and with a single well of a multiwell microplate positioned between them. The conical beam of light emitted by the LED after passing through the aperture is indicated by the V-shaped lines. The height (h) and diameter (d) of the aperture are also indicated.

FIG. 3 shows a collimation means in a preferred embodiment of the microplate reader. An opaque plate (3) containing a plurality of apertures is mounted between the said LEDs and the sample-containing microplate (2). The said apertures are centered over the beams of light (1) emitted by the LEDs. In an especially preferred embodiment, the apertures are cylindrical and the ratio of the heights (h) of the cylindrical apertures to their diameters (d) is from approximately 4 to about approximately 7.5. In an especially preferred embodiment of the said microplate reader, the diameters of the said apertures are between 0.05 and 0.07 inches. As a convenience in manufacturing the said microplate reader, the said plate containing the said type of aperture can also function as a means of holding and positioning the said LEDs.

Figure 4:
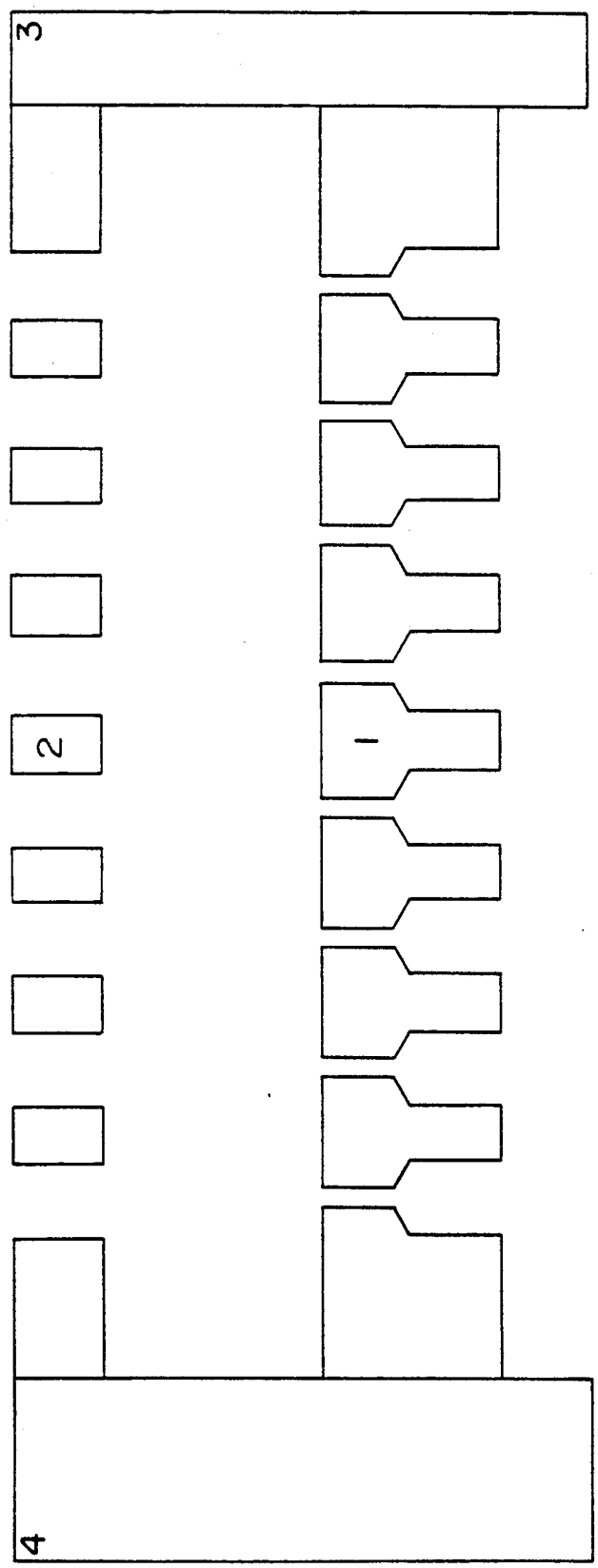
FIG. 4 is a cross-sectional view through one row of the array of mounting holes to accomodate the LED-photodiode pairs, showing the spatial arrangement of the said pairs of the array.
Figure 5:
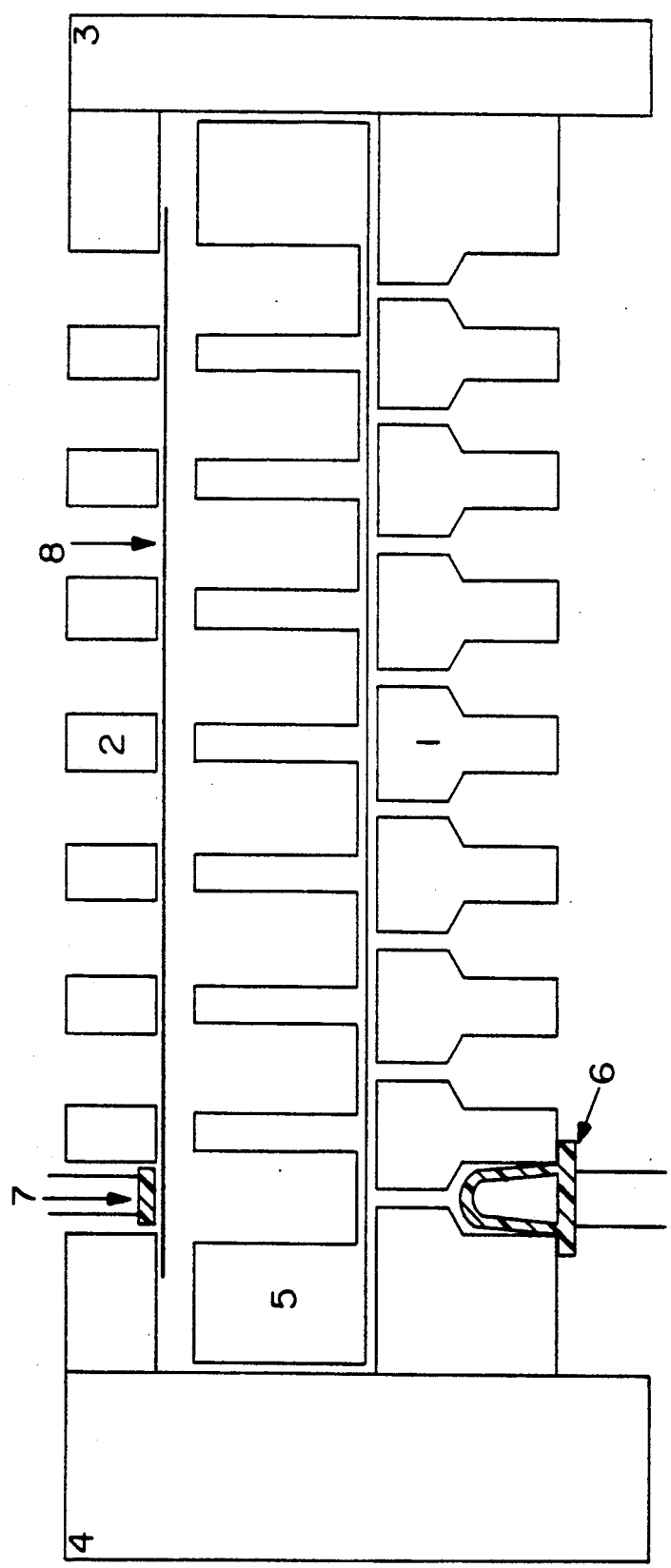
FIG. 5 is a cross-sectional view through one row of the array of mounting holes, as in FIG. 3, with the addition of one LED-photodiode pair and with a multiwell microplate positioned between the LED array and the photodiode array.

FIGS. 4 and 5 show a cross-section of the said microplate reader through a row of the array of LED-photodiode pairs. The combined LED and holding aperture plate (1) properly positions the LED members directly below the photodiode members, which are positioned by a second holding plate (2). Front (3) and back (4) sidewalls support the holding plates and create a space in which the sample-containing microplate (5) may be reversible inserted. One LED (6) and one photodiode (7) of a pair are also shown inserted in place.

In a preferred embodiment of the said microplate reader, an optical cutoff filter (8) is also mounted between the said LEDs and the said photodetectors. The said filter functions to avoid the so-called polychromatic error effect. Polychromatic error is an inaccuracy in the measurement of absorbance caused by the use of an exciting light source of a wavelength bandwidth disproportionate to the wavelength bandwidth of the absorbing chromophore. Polychromatic error is minimized when the variability of the absorptivity of the absorbing chromophore over the range of wavelengths emitted by the source is minimized, i.e., when the chromophore absorptivity is constant over all the wavelengths of light emitted by the source which are registered by the photodetector, the polychromatic error is zero. As the variability in the approximately Gaussian-distribution wavelength range of a light source such as an LED is greatest at both the leading and trailing edges of the LED emission spectrum, and as the LED emission is most asymmetrical at the trailing edge, application of a cutoff filter at this trailing edge of the emission spectrum of the LED will be most useful. In an instrument employing green LEDs exhibiting a dominant wavelength of between 550 nm and 570 nm, a preferred filter is a ROSCOLENE (TM) 874, having long-wavelength cutoff characteristics such that the transmittance at 580 nm is only about 10%, and the transmittance at 600 nm is less than 5%, of the transmittance at 550 nm (set arbitrarily to 100%).

A further aspect of this invention comprises a light-excluding door and an ejector mechanism. Because of the low light output of the LEDs, exclusion of stray ambient light is significant. In a preferred embodiment, shown in FIGS. 6 and 7, the microplate is inserted into the space between the bottom holder-aperture plate (1) and the top holder plate (2), and its lateral positioning is restricted by the side walls (3) and (4). Upon full insertion, the full edge of the microplate encounters the pivot plate (5) upon which is mounted a pivot pin (7) and an ejection lever (9). The entry of the rear edge of the microplate causes the ejection lever (9) to turn about the pivot pin until the long axis of the lever (9) is parallel to the pivot plate (5). The outer end of the ejection lever (9) then projects through a slot in the lateral support wall ((4) in FIG. 5). While pivoting, the ejection lever (9) is free to turn until it contacts the rear wall (6) because a slot (8) is provided to accomodate the lever end.

The opening of the front of the instrument through which the microplate is inserted is closed by means of a band of flexible opaque material (11). In a preferred embodiment, the said band is made of black polymeric fluorocarbon material (e.g., "Teflon"). The band (11) travels in a channel (10) which extends from the front opening at the right side (3) all the way around the left side (4) and the back (6). The band is the length of the left side (4) and back (6). The band may be slid forward to completely cover the front opening through which the microplate is inserted.

A small block of rectangular cross-section is attached to the inner surface of the band (11). The block slides in the rectangular groove (4) which extends the length of the channel (10). The block is fastened to the band (11) at a position such that it just contacts the lever (9) when the right edge of the band (9) clears the left edge of the opening through which the microplate is inserted. The contact with the block causes the lever (9) to pivot around the pin (7), thereby pushing the microplate out through the front opening to facilitate its removal.

Figure 8:
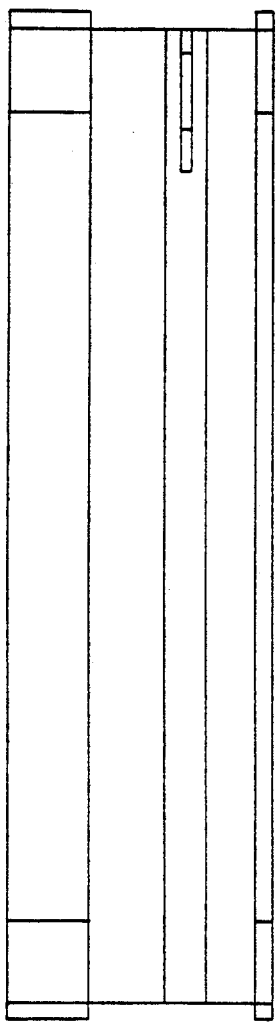
FIG. 8 is a lateral cross-sectional view of the microplate reader, looking from the side and showing the exterior retainer.
Figure 6:
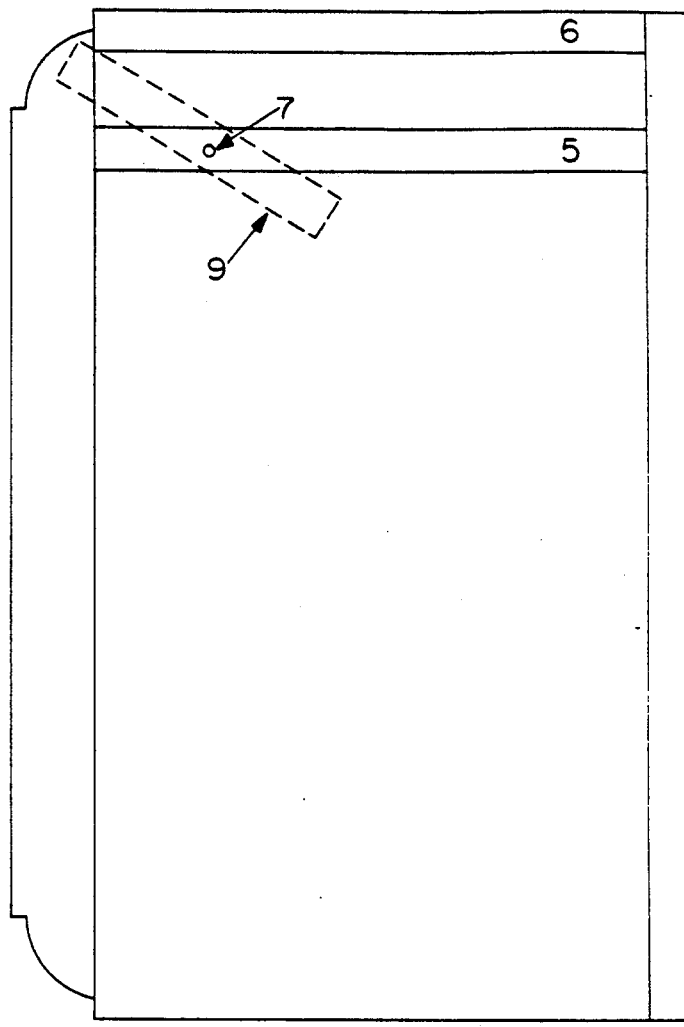
FIG. 6 is a top view of the microplate reader with the rear wall at the top, showing the lever ejection mechanism.
Figure 7:
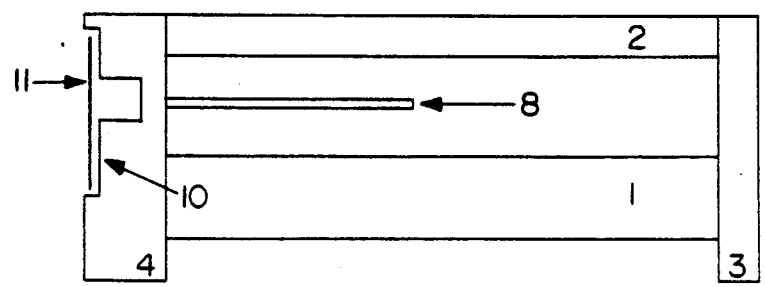
FIG. 7 is a lateral cross-sectional view of the microplate reader, looking from the front, showing the exterior retainer.
Figure 11:
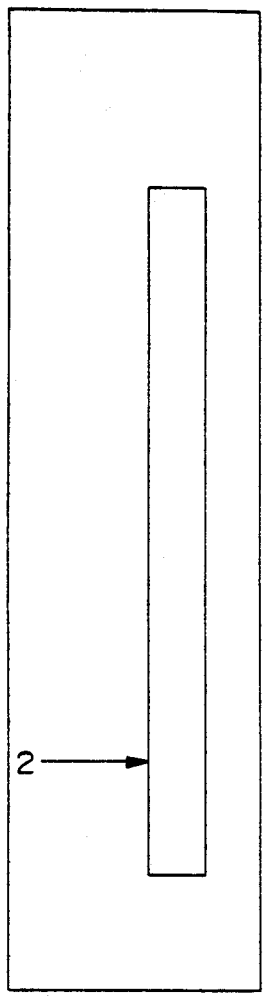
FIG. 11 is a front view of a portion of the exterior retainer, showing the microplate access port.
Figure 9:
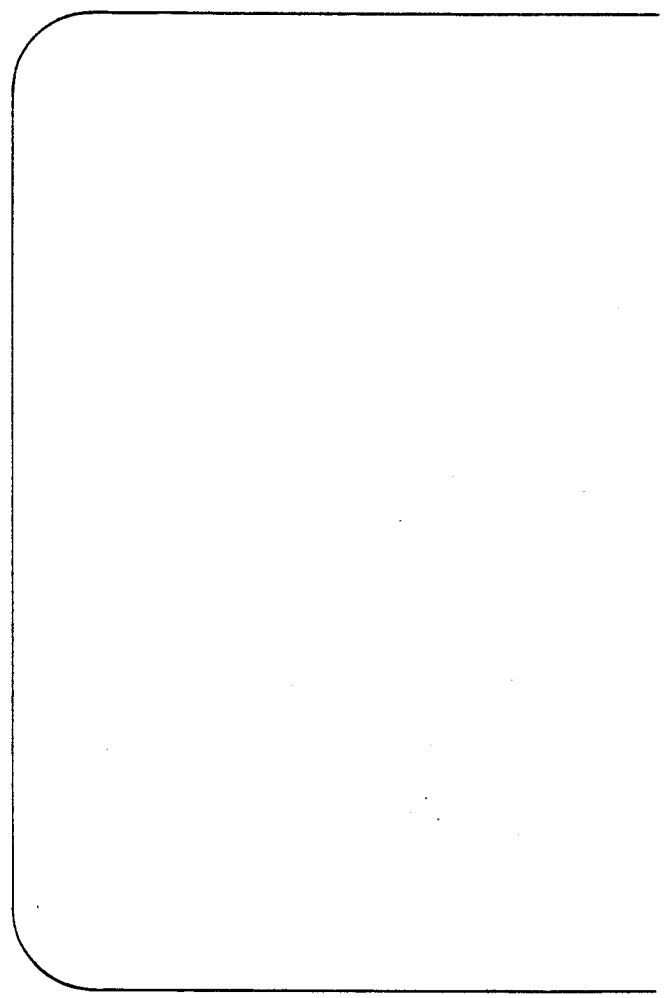
FIG. 9 is a top view of the exterior retainer molded to fit the front, rear, and left side of the microplate reader.
Figure 10:
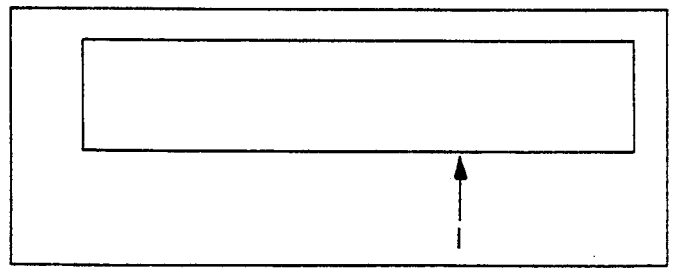
FIG. 10 is a left-side view of a portion of the exterior retainer, showing the knob port.

The sliding band (11) is held in place by an exterior retainer shown in FIG. 9, which is molded to fit the contour of the microplate holder shown in FIGS. 6, 7, and 8. Two rectangular ports are cut into the exterior retainer: a microplate access port, shown in FIG. 10; and a knob port, shown in FIG. 11. The microplate is inserted into the microplate holder through the access port in the front of the microplate reader. To open or close the door of the microplate, the operator moves the knob (attached to the sliding band (11)) through the knob port.

A further aspect of this invention provides a process for generating a chromophore in ELISAs, which chromophore is especially suitable for use with the said microplate reader using a green LED. Peroxidase is a widely used chromogenic enzyme for ELISAs. In practice, various substrates are added to the ELISA reaction solution and are oxidized by peroxidase in the presence of peroxide to generate chromophores. Conventional substrate chromophores include 3,3′,5,5′-tetramethylbenzidine (TMB), o-phenylenediamine (OPD), or 2,2′-azino-bis(3-ethylbenzothiazoline-6-sulfonic acid) (ABTS). The process of this invention comprises incubating peroxidase with a conventional substrate to produce a chromophore, then adding a coupling reagent to generate a new chromophore with an absorption maximum in the green region of the visible spectrum. Two coupling reagents may be used: N,N,N′,N′-tetramethyl-p-phenylenediamine (TMPD) and 3,3′-dimethylnaphthidine (MNAP). In one preferred embodiment comprising a kit, 0.1 ml of a solution of 10 mM TMPD dihydrochloride in 10 mM HCl is added to 0.1 ml of a fully developed ELISA reaction solution containing: 1 nM peroxidase, 50 mM potassium acetate, 2 mM hydrogen peroxide, and 0.5 mM TMB, pH. 4.5, resulting in a violet chromophore with maximal absorption around 560 nm. In another embodiment, the said ELISA reaction mixture is reacted with 0.1 ml of a solution of 1 mM MNAP containing 0.2M HCl and 50% acetic acid, resulting in a red-violet chromophore with maximal absorption near 550 nm. In the first kit, the blue-green TMB chromophore is changed to the blue-violet TMPD chromophore; in the second kit, the blue-green TMB chromophore is changed to the red-violet MNAP chromophore.

We claim:

1. An optoelectronic instrument for measuring the absorbance of a plurality of samples, comprising:
   a plurality of LED-photodetector pairs, each of the said pairs being internally aligned so that light emitted by the said LED member is directed toward the photoreceptive surface of the corresponding said photodetector member of said pair, the said plurality of LED-photodetector pairs being arranged to form a spatial array of adjacent pairs,
   means for removably positioning said plurality of samples so that each said sample is positioned between the said LED member and the said corresponding photodetector member of a said pair, so that the light from the LED member of such pair passes through the said sample before striking the said photodetector member of said pair,
   electronic means for sequentially pulsing the LED members of said array, said sequential pulsing occurring in a sequence such that when absorbance of any particular said sample is being measured, the particular said LED member which corresponds to the said particular sample emits light, while said LED members which correspond to samples adjacent to said particular sample do not emit light simultaneously with said particular LED member, and
   electronic means for sequentially measuring the signal from each said photodetector during the interval in which its corresponding said LED member is emitting light, and calculating the absorbance or transmittance of corresponding said sample.

2. The optoelectronic instrument of claim 1, wherein the said spatial array of adjacent LED-photodiode pairs is adapted to measure the said plurality of samples contained in a multiwell microplate.

3. The optoelectronic instrument of claim 2, wherein the light emitted from each LED member is collimated through a cylindrical aperture, each said aperture having a height-to-diameter ratio of between approximately 4 and approximately 7.5.

4. The optoelectronic instrument of claim 3, wherein each said aperture has a diameter of between approximately 0.05 and 0.07 inches.

5. The optoelectronic instrument of claim 2, comprising in addition a long-wavelength cutoff filter means adapted to minimizing polychromatic error, said filter means being interposed between the LED members and photodetector means.

6. The optoelectronic instrument of claim 5, wherein the plurality of LED embers are green LEDs exhibiting a dominant wavelength of between 550 nm and 570 nm, and the filter means is a (Roscolene) ROSCOLENE (TM) 874 or other filter having transmittance at 600 nm which is less than 5% of the transmittance at 550 nm.

7. An optoelectronic instrument as in claim 1, wherein said photodetectors are photodiodes having integral infrared filters covering their photoreceptive surfaces.

8. An optoelectronic instrument as in claim 2, wherein said plurality of LED members is mounted below said multiwell microplate and said plurality of photodetector members is mounted above said multiwell microplate.

9. An optoelectronic instrument as in claim 1, wherein said means for reversibly positioning said plurality of samples comprises a light-excluding door and an ejector mechanism, said door being a band of opaque flexible material adapted to slide in a channel, said channel extending partially around the lateral perimeter of said instrument and past an opening adapted to receive a sample plate containing said plurality of samples, said band being at least as long as said opening, said band having attached to its inner surface a means for contacting and activating said ejection mechanism when said door is opened, said ejection mechanism being adapted to eject said sample plate through said opening.

10. An optoelectronic instrument as in claim 9, wherein said opaque flexible material comprises fluorocarbon polymeric material.

11. An optoelectronic instrument as in claim 1, wherein the said signal in analog form from each said photodetector is attenuated by an attenuator device prior to being digitized by an analog-to-digital converter, said attenuation comprising the steps:
   a) obtaining the full scale analog current signal from each said LED-photodetector pair with said LED emitting light in the absence of sample;
   b) converting said full scale analog current signal to a full scale analog voltage signal by means of a current to voltage converter;
   c) applying said full scale analog voltage signal to said attenuator device;
   d) determining for each said LED-photodetector pair an attenuator constant such that the combination of said attenuator constant with said full scale analog voltage signal within said attenuator device produces a voltage output signal having a predetermined value less than but close to the maximum input signal for said analog to digital converter;

e) storing each said attenuator constant corresponding to each said LED-photodetector pair in an attenuator table in a computer memory;
f) restoring each said attenuator constant to said attenuator device when signal from said corresponding LED-photodetector pair is being measured; and
g) combining each said signal with said corresponding restored attenuator constant within said attenuator device and passing the resulting output from said attenuator device to said analog to digital converter.

12. An optoelectronic instrument as in claim 1, wherein the light output from said LEDs is stabilized by applying a heating pulse at intervals between measuring pulses to each said LED to be stabilized, said heating pulses preferably having a power level, interval, and duration chosen such that the time average power of said heating pulses is approximately equal to the time average power of said measuring pulses.

* * * * *